US007674590B2

(12) United States Patent
Chen

(10) Patent No.: US 7,674,590 B2
(45) Date of Patent: Mar. 9, 2010

(54) METHODS FOR DIAGNOSING AND FOR MONITORING THE TREATMENT OF RECURRENT SPONTANEOUS ABORTION

(75) Inventor: Fenglin Chen, Beijing (CN)

(73) Assignee: Beijing Xinjing Antai Medical and Technology Service Limited Corp., Beijing (CN)

( * ) Notice: Subject to any disclaimer, the term of this patent is extended or adjusted under 35 U.S.C. 154(b) by 304 days.

(21) Appl. No.: 10/586,285

(22) PCT Filed: Feb. 20, 2004

(86) PCT No.: PCT/CN2004/000134

§ 371 (c)(1),
(2), (4) Date: Jul. 13, 2006

(87) PCT Pub. No.: WO2005/080980

PCT Pub. Date: Sep. 1, 2005

(65) Prior Publication Data

US 2007/0160997 A1 Jul. 12, 2007

(51) Int. Cl.
*G01N 33/53* (2006.01)
*G01N 33/543* (2006.01)
(52) U.S. Cl. .................. 435/7.1; 435/7.21; 436/501; 436/518; 422/50; 422/60; 422/61
(58) Field of Classification Search .................. None
See application file for complete search history.

(56) References Cited

U.S. PATENT DOCUMENTS

| 4,444,879 | A | * | 4/1984 | Foster et al. .................. 435/7.95 |
| 5,281,522 | A | | 1/1994 | Senyei et al. |
| 5,468,619 | A | | 11/1995 | Senyei et al. |

FOREIGN PATENT DOCUMENTS

| DE | 28 36 362 | 3/1980 |
| JP | 9-218202 | 8/1997 |
| WO | 83/00877 | 3/1983 |
| WO | 02/42769 | 5/2002 |

OTHER PUBLICATIONS

Ogasawara et al. (Lancet, vol. 347, Apr. 27, 1996, pp. 1183-1184).*
Bernasconi et al. (American Journal of Human Genetics, 1996, vol. 59, No. 5 pp. 1114-1118).*
Maggio (Immunoenzyme technique I, CRC press ã 1980, pp. 186-187).*
Aoki et al. (American Journal of Reproductive Immunology, 1993, vol. 29, pp. 82-87).*
Jones (Acta Endocrinologica, 1975, vol. 78, No.Suppl94, pp. 376-404, Abstract Only).*
Kwak et al. (Journal of Reproductive Immunology, 1995, vol. 28, pp. 175-188).*
Perdriger et al., "The genetic basis for systemic lupus erythematosus"., Joint Bone Spine, vol. 70, 2003, pp. 103-108.*

English Abstract: American Chemical Society. Ogasawara, M. et al. "Clinical Significance of β2 Glycoprotein I Dependent Ancicardiolipin Antibody, Lupus Anticoagulant and Antinuclear Antibodies in Patients with Recurrent Miscarriages" *Reproductive Immunology* (1998) vol. 10, pp. 272-276.
English Abstract: American Chemical Society. Kano, T. et al. "The Incidence of Endometriosis and Adenomyosis in Patients with Habitual Abortion in Relation to Immunological Abnormalities" *Nippon Funin Gakkai Zasshi* (1997) vol. 42, No. 2 , pp. 113-118.
Pandey, M. K., et al "Lymphocyte immunotherapy and its probably mechanism in the maintenance of pregnancy in women with recurrent spontaneous abortion" *Archives of Gynecology and Obstetrics, Springer Verlag*, Berlin DE, (2004) vol. 269, pp. 164-165.
Stricker, R. B., et al "Successful treatment of immunologic abortion with low-dose intravenous immunoglobin" *Fertility and Sterility, Elsevier Science Inc*, (2000) vol. 73, pp. 538-540.
Gafter, U. et al "Suppressed cell-mediated immunity and monocyte and natural killer cell activity following allogeneic immunization of women with spontaneous recurrent abortion" *Journal of Clinical Immunology, Plenum Publishing Co*, (1997) vol. 17, pp. 415-418.
Ogasawara M., et al "Are antinuclear antibodies predictive of recurrent miscarriage?" (1996) vol. 347 pp. 1183-1184.
Ksouri, H., et al. "Recurrent pregnancy loss related to immune disorders." *Ann Med Interne* (Paris) (2003) vol. 154, No. 4, pp. 233-247.
Gatenby, P. A., et al. "Treatment of recurrent spontaneous abortion by immunization with paternal lymphocytes." *Am. J. Reprod. Immunol* (1993) vol. 29, No. 2, pp. 88-94.
Review Article"Recurrent Pregnancy Losses and the Role of Immunotherapy." *Arch Gynecol Obstet* (2000) vol. 264, pp. 3-12.
Feinberg, R. F., et al. "Is Oncofetal Fibronectin a Trophoblast Glue for Human . . . ?" *American Journal of Pathology* (1991) vol. 138, No. 3,.
Chakraborty, C., et al. Regulation of human trophoblast migration and invasiveness.: *Can J Physiol Pharmacol.* (2002) vol, 80, No. 2, pp. 116-124.
Koenn, M. E., et al. "Fetal Fibronectin." *Clin Lab Sci* (2002) vol. 15, No. 2, pp. 96-98, 115.
U.S. Appl. No. 10/585,623, filed Jul. 2006, Chen.
Ramhorst, R. et al. "Intracellular expression of CD69 is endometrial and peripheral T cells . . . leukocyte immunotherapy." American Journal of Reproductive Immunology (2003) vol. 49, pp. 149-158.

* cited by examiner

*Primary Examiner*—Lisa V Cook
(74) *Attorney, Agent, or Firm*—Ladas & Parry LLP

(57) ABSTRACT

The present invention discloses a method of diagnosis of immunological recurrent spontaneous abortion. The level of antinuclear antibody in a body fluid of a patient is determined and determined level is compared to the level of corresponding antinuclear antibody of a control. Particularly, isolated chromosome No. 2 or fragment thereof including fibronectin encoding gene derived from male(s) is used as antigen in the method of the present invention for determining the level of corresponding antinuclear antibody in a body fluid sample of the patient. The present invention also discloses a diagnostic kit for immunological recurrent spontaneous abortion, and method and kits for monitoring the therapeutic effect for immunological recurrent spontaneous abortion.

2 Claims, 2 Drawing Sheets

METHODS FOR DIAGNOSING AND FOR MONITORING THE TREATMENT OF RECURRENT SPONTANEOUS ABORTION

This is a 35 USC 371 of PCT/CN2004/000135.

FIELD OF THE INVENTION

The present invention relates to methods for diagnosing and for monitoring the treatment of recurrent spontaneous abortion.

BACKGROUND OF THE INVENTION

Abortion is the termination of pregnancy before the 28th gestational week characterized by expulsion of the fetus and attachments thereof from a pregnant woman. Recurrent spontaneous abortion (RSA) refers to the phenomenon of two or more consecutive abortions characterized by the termination of fetal development in the same gestational week. Recurrent spontaneous abortion affects 2-3% of pregnant women. Recurrent spontaneous abortion can be classified into early recurrent spontaneous abortion (before the 12th gestational week) and late recurrent spontaneous abortion (after the 12th gestational week) based upon its occurring time. Recurrent spontaneous abortion can also be classified into primary recurrent spontaneous abortion and secondary recurrent spontaneous abortion based upon whether there is a normal pregnancy history before the abortion. Clinically, RSAs are divided into early primary RSA, late primary RSA, early secondary RSA and late secondary RSA based upon the two kinds of classification set forth above.

RSAs can be resulted from many causes including abnormity of chromosome, endocrine imbalance, anatomical abnormality of reproduction organs, bacterial infection, viral infection, blood group incompatibility between mother and fetus and environmental pollution, etc. About half of RSAs still have no known cause, and are called unexplained RSAs. Along with the deep understanding of reproductive immunology and the development of immunological assays, immunological factors are thought to be the main cause of unexplained RSAs (Ksouri H, Zitouni M, Achour W, Makni S, Ben Hassen A., Recurrent pregnancy loss related to immune disorders, Ann Med Interne (Paris). 2003 September; 154(4): 233-47.). RSAs associated with immunological factors are called immunological RSAs.

There are several representative hypotheses about the immunological mechanism of RSA, for example: (1) production of the blocking antibodies (BA), such as anti-paternal cytotoxic antibodies (APCA), anti-idiotypic antibodies (Ab2) and mixed lymphocyte reaction blocking antibodies (MLR-Bf) which can inhibit the attack to fetus by maternal immunological system, is inhibited due to the increased sharing of human leukocyte antigens (HLA) between the couple; (2) overactivity of helper T cell 1 (Th1)-derived cytokines and of natural killer cells (NK); (3) abnormal increase of antiphosphokipid antibodies (APA). APA is a group of autoimmune antibodies including anticardiolipin (aCL) antibodies and lupus anticoagulants, etc.

Of the methods for treating immunological RSA, lymphocyte immunotherapy is currently popular. This immunotherapy of RSA has been applied both in China and other countries since Taylor and Faulk infused to a patient of unexplained RSA a suspension of mixed leukocytes derived from her spouse in 1981 (Gatenby P A, Cameron K, Simes R J. Treatment of recurrent spontaneous abortion by immunization with paternal lymphocytes: results of a controlled trial. Am J Reprod Immunol. 1993 March; 29(2): 88-94.). The immunogen is lymphocytes from the spouse in most cases. The immunotherapy includes isolating lymphocytes from the spouse's venous blood for intracutaneous injection. Alternatively, the condensed leucocytes or whole blood from the spouse can also be intravenously injected. If the live cells are inactivated by 200rad X-ray radiation prior to intracutaneous injection, the graft-versus-host reaction can be attenuated. Usually, the immunization is performed every 2 weeks for a total of 2 to 4 times before pregnancy and boosted 1 to 3 times after pregnancy. Twenty years after the application of lymphocyte immunotherapy for treating RSA, a great deal of studies from China and other countries have indicated that the therapeutic effect of this therapy is not definite and the therapy has some serious adverse side effects. Therefore, it should be applied cautiously (Recurrent Pregnancy Losses and the Role of Immunotherapy. Review Article, Arch Gynecol Obstet (2000) 264:3-12).

The inventor of the present invention has studied in-depth on the immune recognition mechanism between pregnant woman and her fetus as well as the immunological pathogenesis of pathological pregnancy, and has found the pathological changes and the etiology of unexplained early secondary RSA. An efficient and safe immunotherapy of RSA is provided based upon this finding (see the gene vaccine therapy disclosed in another PCT application filed on the same day by the applicant of the present invention). This therapy had been applied in a preliminary clinical trial in which more than 300 cases were included. The cure rate is more than 95% and no side effect has been found.

Since the above gene vaccine therapy is only effective for immunological RSA, there is a need for a quick and simple diagnostic method of immunological RSA to improve the specificity and effectiveness of the therapy. In addition, there is a need for a method for monitoring the therapeutic effect in the course of treatment to determine the time for safe conception and ensure that the gestation will pass through the gestational phase when abortion used to happen.

Antinuclear antibodies (ANAs) generally refer to antibodies in serum against various nuclear components including anti-nucleic acid antibodies and anti-nucleoprotein antibodies. ANAs widely exist in various autoimmune diseases. Therefore, ANA assay is a main item of laboratory examination for diagnosing autoimmune diseases such as systemic lupus erythematosus and Sjogren syndrome etc.

The commonly used ANA assays include indirect immunofluorescence, enzyme linked immunosorbent assay (ELISA) and the like. The antigens used are primate liver, Hep-2 cells or various purified nuclear antigens etc.

SUMMARY OF THE INVENTION

In order to diagnose immunological RSA quickly and monitor the effect of immunological therapy, the present invention provides:

1. A method of diagnosis of immunological recurrent spontaneous abortion, characterized by in vitro determining the level of antinuclear antibody in a body fluid sample of a patient and comparing the result with the level of corresponding antinuclear antibody of normal control.

2. The method of diagnosis according to 1, wherein a mixture of isolated chromosome No. 2 or fragment thereof containing fibronectin encoding gene derived from a plurality of males is used as antigen for determining the level of corresponding antinuclear antibody in the body fluid sample of the patient.

3. The method of diagnosis according to 1, wherein isolated chromosome No. 2 or fragment thereof containing fibronectin encoding gene derived from the spouse of the patient is used as antigen for determining the level of corresponding antinuclear antibody in the body fluid sample of the patient.

4. A kit for the diagnosis of immunological recurrent spontaneous abortion, comprising chromosome No. 2 or fragment thereof containing fibronectin encoding gene derived from male(s) as antigen.

5. The kit according to 4, wherein said male is the spouse of the patient.

6. The kit according to 4, wherein said males are a plurality of males arbitrarily chosen.

7. The kit according to 4 to 6, wherein said antigen is coated on a solid carrier.

8. The kit according to 4 to 7, further comprising enzyme-labeled secondary antibody, necessary buffer and operation instructions.

9. A method for monitoring the therapeutic effect of immunological recurrent spontaneous abortion, characterized by in vitro determining the level of antinuclear antibody in a body fluid sample of a patient having received treatment and comparing the result with the level of antinuclear antibody before treatment.

10. A kit for monitoring the therapeutic effect of immunological recurrent spontaneous abortion, comprising chromosome No. 2 or fragment thereof containing fibronectin encoding gene derived from male(s) as antigen.

DETAILED DESCRIPTION OF THE INVENTION

The inventor of the present invention has carried out a clinical epidemiological study on early secondary RSA. It has been found that among various factors concerned, artificial abortion has the highest correlation with early secondary RSA, most of which happened on the same or almost the same gestational week when the previous artificial abortion was made. There is statistically significant difference between the group of early secondary RSA and the control group (see table 1). Therefore, the inventor of the present invention deduced that artificial abortion was the inducing cause of early secondary RSA.

TABLE 1

Epidemiological investigation on early secondary RSA

| Item | Number of cases (N) | Artificial abortion Number of cases (N) | Percentage (%) | Consistency of timing Number of cases (N) | Percentage (%) |
|---|---|---|---|---|---|
| RSA | 35 | 32 | 91 | 30 | 86 |
| Control | 140 | 28 | 20 | — | — |
| ×2 | | 52.4 | | | |
| P | | <0.01 | | | |

In order to explore the pathogenesis of early secondary RSA, the inventor of the present invention had monitored the repregnancy of early secondary RSA patients having a history of artificial abortion. When the cessation of fetal development was observed, conceptus samples with intact placental villi were obtained through drug abortion from RSA patients. The conceptus samples from subjects without RSA were used as control. The collected conceptus samples were observed under microscope and scanning electron microscope and studied by immunohistochemistry assay. It was found that there was no difference between the structures of the placental villi of the two groups under microscope. But under scanning electron microscope, it was found that there was a layer of dense protein net outside the trophocytes of control samples (see FIG. 1) while the trophocytes of RSA samples were naked (see FIGS. 1 and 2). Results of the immunohistochemistry assay demonstrated that there was a fibronectin band between the trophocytes and deciduas and among the trophocytes per se of the control samples, while there was no fibronectin outside the trophocytes of the RSA's samples. Accordingly, the inventor of the present invention hypothesized that the fibronectin band outside trophocytes was the main component of placental immunological barrier, and that impairment of the immunological barrier resulted from the loss of the fibronectin band was the cause of immunological RSA.

In order to find the reason of the loss of the fibronectin band outside the trophocytes of immunological RSA patients, the inventor of the present invention measured the level of anti-FN antibody in serum of 30 subjects suffered from early secondary RSA with a history of artificial abortion by using an anti-FN antibody detection kit. There was no statistical difference between the experimental group and the control group. Surprisingly, the inventor found that the level of antinuclear antibody against chromosome No. 2 (containing FN encoding gene) in the sera of the patients (detected according to the method described in Example 2) was significantly higher than that of the control group (see table 2).

Accordingly, the inventor put forward a hypothesis about the pathogenesis of immunological RSA: during the artificial interference in pregnancy such as artificial abortion, the fetal cells are broken and the expressing FN encoding gene originated from the spouse is presented to the maternal immune system as antigen, inducing the appearance of antinuclear antibody against FN encoding gene. When the woman is pregnant again with the same spouse, the antinuclear antibody against FN encoding gene enters into the trophocytes and binds to the expressing FN encoding gene. The FN encoding gene is blocked, therefore the fibronectin band outside the trophocytes can not be formed normally and the integrity of the fetal immunological barrier is impaired. The rejection of the repregnant woman to the fetus results in cessation of fetal development and eventually the abortion.

Fibronctin is a macromolecular multifunctional glycoprotein found in connective tissue, on cell surfaces, in cytoplasma and other body fluids. FN band had been found outside fetal trophocytes. But the FN band was thought only to act in connection between placenta and deciduas (Ronald F. Feinberg, Harvey J. Kliman, and Charles J. Lockwood, Is Oncofetal Fibronectin a Trophoblast Glue for Human Implantation? American Journal of Pathology, Vol. 138, No. 3, March 1991), migration and invasion of trophocytes in decidua (Chakraborty C, Gleeson L M, McKinnon T. Lala P K., Regulation of human trophoblast migration and invasiveness. Can J Physiol Pharmacol. 2002 Feb; 80(2): 116-24. Review.). It was also suggested that the FN level in cervical secrete was indicative of premature labor (Koenn M E., Fetal fibronectin, Clin Lab Sci. 2002 Spring; 15(2):96-8, 115). The action of FN in the fetal immunological barrier has not been recognized in the prior art. Human FN encoding gene was allocated at chromosome 2q34 by autoradiography in 1995.

The inventor of the present invention made further research based upon the above studies about the pathogenesis of immunological RSA in attempt to find an effective method for treating immunological RSA. It is surprisingly found that injection, to a subject suffered from immunological early secondary RSA before pregnancy, of chromosome No. 2 containing FN encoding gene derived from her spouse can effectively lower the level of antinuclear antibody against chromosome No. 2 in peripheral blood of the subject (see table 2). Even surprisingly, subjects suffered from immunological RSA can be prevented from abortion by significantly lowering the level of said antinuclear antibody before or during pregnancy and maintaining the level at a safe level for pregnancy in a certain period of time.

TABLE 2

Change of the level of antinuclear antibody in serum of RSA patients before and after treatment

| | Number of cases | Mean value of the titer of antinuclear antibody in peripheral blood | Difference between groups |
|---|---|---|---|
| Before chromosome treatment | 35 | 1:254.7 | — |
| After chromosome treatment | 35 | 1:34.6 | — |
| Control group | 45 | 1:38.9 | $P < 0.01$ |

Therefore, the present invention has demonstrated that immunological recurrent spontaneous abortion correlates directly to the in vivo level of antinuclear antibody of the patients of immunological RSA.

Accordingly, the present invention provides a method and a kit for diagnosing immunological recurrent spontaneous abortion by in vitro determining the level of antinuclear antibody in a body fluid sample of a patient. The present invention also provides a method and a kit for monitoring the therapeutic effect against immunological recurrent spontaneous abortion by in vitro determining the level of antinuclear antibody in a body fluid sample of a patient having received treatment.

As used herein, the following terms have the meanings as follows:

Subject (patient): any female mammal including human.

Spouse: the sexual partner of the RSA subject responsible for the aborted gestations.

Chromosome No. 2: human chromosome No. 2 or the corresponding chromosome of other mammals containing FN encoding gene. For other mammals, as long as it contains FN encoding gene, the serial number of said chromosome is not necessarily No. 2 in the genome.

Antinuclear antibody: antibodies against various nuclear components, particularly the antibody/antibodies detected according to a method similar to that described in Example 2.

Immunological RSA: early secondary recurrent spontaneous abortion wherein the titer of the antinuclear antibody in serum is higher than 1:64.

Titer (level) of the antibody: the largest diluting factor of sample serum at which the detection of the antibody is still positive by ELISA.

Safe level for pregnancy: the RSA patient's level of antinuclear antibody which is lowered at least by about 30%, preferably at least about 40%, more preferably at least about 50%, 60%, 70% or more, as compared with the original level of the antibody before therapy, or the antibody titer is smaller than about 1:64.

Isolated: chromosome No. 2 is isolated from other cell components (including proteins, other chromosomes, etc.). Preferably, the content of other cell components is less than 10 wt %, more preferably less than 5 wt %, 4 wt %, 3 wt %, 2 wt %, or even less than 1 wt % based upon weight of dry material. Preferably, the content of other chromosomes is less than 10%, more preferably less than 1%.

Fragment of chromosome: a fragment of chromosome No. 2 that contains FN encoding gene and keeps the activity for decreasing the level of antinuclear antibody according to the present invention.

As described above, the present invention relates to a method of diagnosis of immunological recurrent spontaneous abortion characterized by in vitro determining the level of antinuclear antibody in a body fluid sample of a patient and comparing the result with the level of corresponding antinuclear antibody of normal control.

In a preferred embodiment of the diagnosis method of the present invention, a mixture of isolated chromosome No. 2 or fragment thereof containing fibronectin encoding gene derived from a plurality of males is used as antigen for determining the level of corresponding antinuclear antibody in the body fluid sample of the patient. Said plurality of males means, for example, more than 3, preferably more than 5, more preferably more than 10, even more preferably more than 20, and most preferably more than 30 normal males.

In another embodiment of the diagnosis method of the present invention, isolated chromosome No. 2 or fragment thereof containing fibronectin encoding gene derived from the spouse of the patient is used as antigen for determining the level of corresponding antinuclear antibody in the body fluid sample of the patient.

Correspondingly, the present invention relates to a kit for the diagnosis of immunological recurrent spontaneous abortion, comprising chromosome No. 2 or fragment thereof containing fibronectin encoding gene derived from male(s) as antigen.

In an embodiment of the kit of the present invention, the kit comprises chromosome No. 2 or fragment thereof containing febronectin gene derived from the spouse of the patient as antigen.

In a preferred embodiment of the kit of the present invention, the kit comprises a mixture of chromosome No. 2 or fragment thereof containing febronectin gene derived from a plurality of arbitrarily chosen males as antigen. For example, the chromosomes or fragments thereof are derived from more than 3, preferably more than 5, more preferably more than 10, even more preferably more than 20, and most preferably more than 30 normal males.

In the kit of the present invention, said antigen is preferably coated on a solid carrier, which may be any solid carrier commonly used in immune assays, such as a microtiter plate.

In a particularly preferred embodiment of the present invention, said kit further comprises an enzyme-labeled secondary antibody, necessary buffer and operation instructions.

The sample used for determining the level of antinuclear antibody of the patient can be any kind of body fluid, secretion, blood etc. from the patient. Peripheral blood is preferred.

The method for determining the level of antibody can be any suitable method well known to a skilled person in the art. Enzyme linked immunosorbent assay (ELISA) is preferred. The antigen used in the method is preferably a mixture of chromosome No. 2 or fragment thereof containing fibronectin encoding gene derived from a plurality of normal males such as from 30 males. The antigen can be coated on a solid carrier by any method well known to a skilled person in the art. A serial dilutions of the sample to be tested (>1:32) can be prepared. Preferably the diluting factor is in the range of 1:64 to 1:1024. The reaction is carried out at 37° C. for 20 to 40 minutes, preferably 30 minutes. The secondary antibody is anti-human IgG antibody which can be derived from rat, mouse, goat, rabbit etc. The enzyme for labeling the secondary antibody can be any one selected from horse radish peroxidase, akaline phosphatase, superoxide dismutase and the like. The coloring agent can be any enzyme substrate which does not produce any deposit. TMB (3,3',5,5'-tetramethylbenzidine) and ABST are preferred. Results can be observed by naked eye directly or OD value is determined by means of a microplate reader. If the result is positive when the dilution factor is larger than 1:64, it is significant for clinical diagnosis.

For example, a method of treatment of RSA is as follows. Chromosome No. 2 or fragment thereof is isolated from peripheral blood of the spouse of the patient by an ordinary method, and is mixed with sterile water for injection or physiological saline to obtain an injection solution. The concentration of chromosome is for example about 10 per field of oil immersion objective. The solution is generally injected subcutaneously to the patient for 0.5 to 2.0 ml each time. The injection is generally performed 3 to 5 times, preferably 4 times during 30 days for each course of treatment. When one course of treatment is finished, the level of antinuclear antibody in peripheral blood is determined. If the level of the antibody is lowered down to the extent that is safe for gestation, the patient is ready for pregnancy. For example, after one course of treatment, the level of antinuclear antibody safe for gestation can be maintained for about 3 months during which the patient can safely become pregnant.

After the gene vaccine derived from the spouse is injected, the change of the level of specific antinuclear antibody of the patient is determined to assess the therapeutic effect and to instruct the patient of proper time for conception. When the level of antinuclear antibody is lowered by at least about 30%, preferably at least about 40%, more preferably at least about 50% compared with the level of antinuclear antibody before treatment, or the antibody titer is lower than 1:64, it is the range for safe conception and normal pregnancy becomes possible. After conception, another course of treatment by the gene vaccine is usually performed, and the level of antinuclear antibody of the patient is monitored at the same time to keep it in the normal range so as to make gestation pass through the gestation stage when abortion used to occur.

Accordingly, the present invention also relates to a method for monitoring the therapeutic effect for immunological recurrent spontaneous abortion, characterized by in vitro determining the level of antinuclear antibody in a body fluid sample from the patient having received treatment and comparing the result with the level before treatment.

Correspondingly, the present invention also relates to a kit for monitoring the therapeutic effect for immunological recurrent spontaneous abortion. The kit comprises isolated chromosome No. 2 or fragment thereof containing fibronectin encoding gene derived from male(s) as antigen.

The above description and preferred conditions of the diagnostic method and kit of the present invention also apply to the method and kit for monitoring the therapeutic effect of the present invention.

300 cases of immunological RSA have been diagnosed by the method of diagnosis of the present invention considering the medical history. Immunotherapy has been performed on each patient by injecting a preparation containing chromosome No. 2 derived from the spouse of the patient. The cure rate is up to 95%. Therefore, determination of antinuclear antibody provides an objective and accurate diagnostic criterion for immunological RSA.

The present invention is further illustrated by the drawings and specific examples which are not intended to limit the scope of the present invention.

EMBODIMENTS OF THE INVENTION

EXAMPLE 1

Loss of the fibronectin band outside the fetal trophocytes in early secondary RSA cases (1) A number of early secondary RSA patients with a history of artificial abortion were monitored when they got pregnant again. When the termination of fetal development was detected, fetus samples of RSA with intact placental villus were obtained by drug abortion.

(2) Fetus samples from subjects without a history of RSA were obtained by drug abortion and used as control.

(3) Placenta samples were fixed by 10% neutral formalin, dehydrated, embedded in paraffin, sliced to 4-5 μm tissue slices, and stained with HE. It was observed that there was no significant difference between the two groups of placental tissue under microscope.

Figure 1:
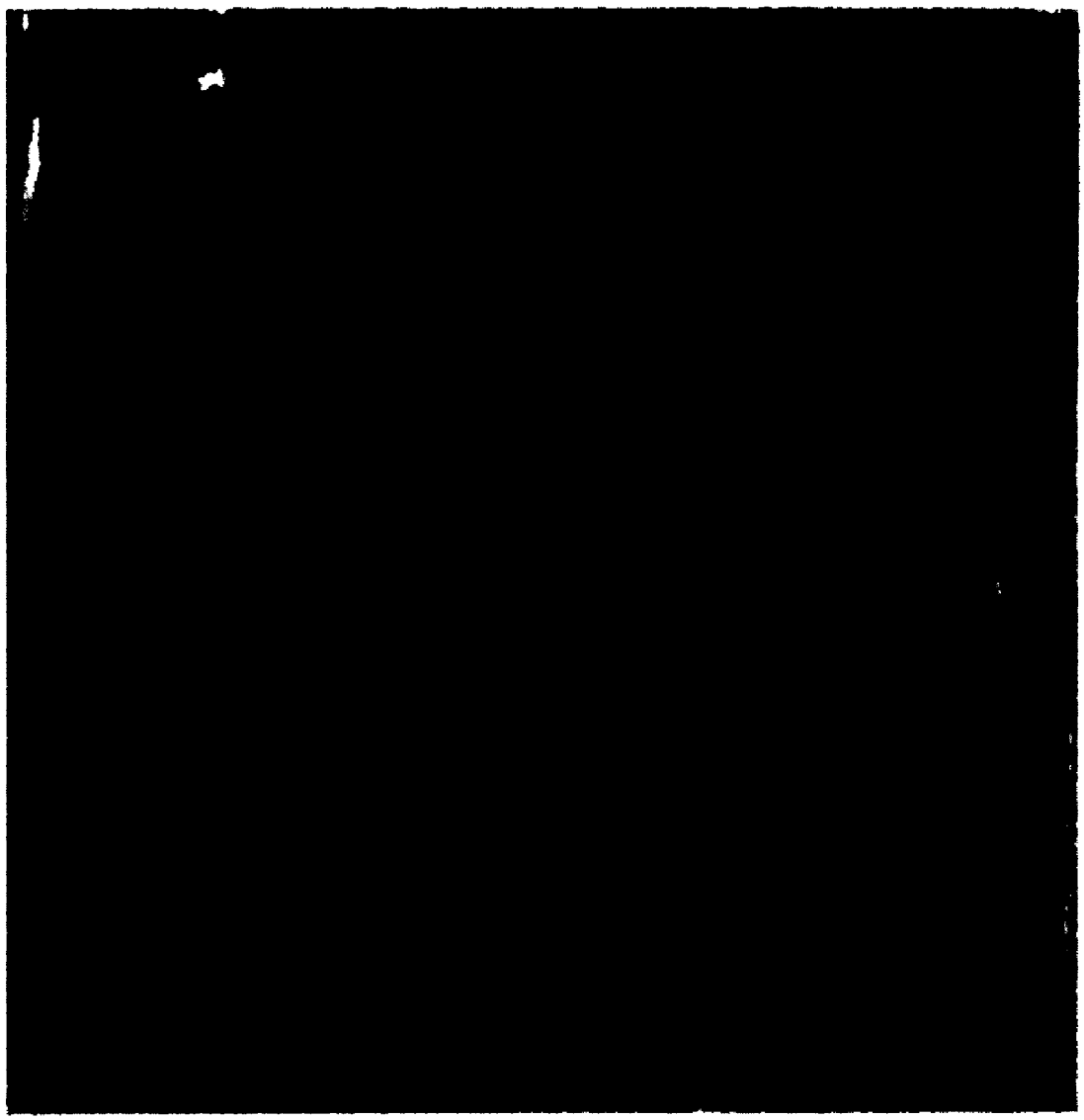
FIG. 1 is a photo of normal placenta of control sample under scanning electron microscope. It can be observed that there is a layer of dense protein net outside the trophocytes.
Figure 2:
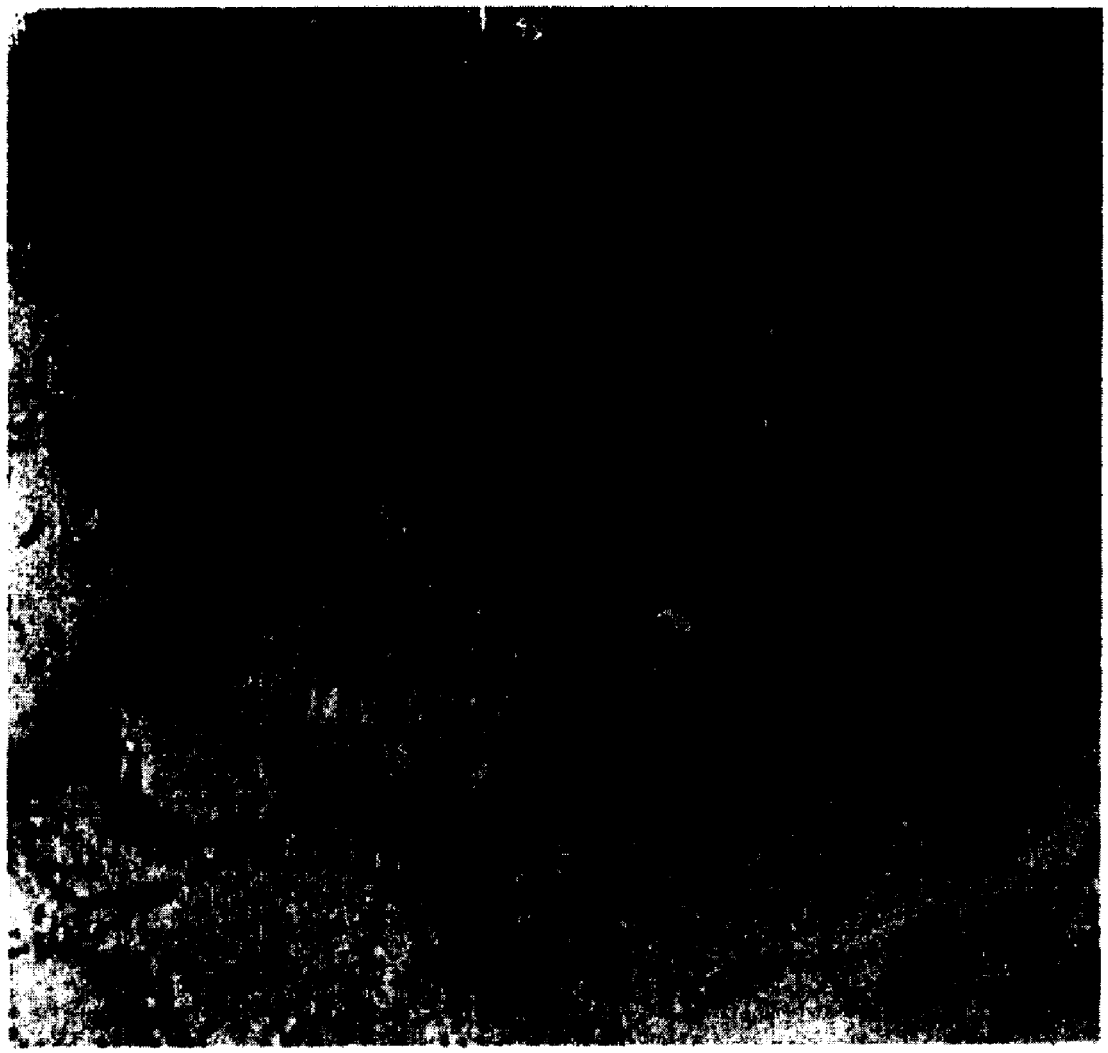
FIG. 2 is a photo of RSA patient's placenta sample under scanning electron microscope. It can be observed that the trophocytes are naked.

(4) Fresh placenta samples were fixed by 2.5% glutaraldehyde and made into slices by a conventional method to observe under transmission electron microscope. It was found that there was a dense protein net outside the trophocytes of control samples, while the trophocytes of the RSA patients' samples were naked. The results are shown in FIGS. 1 and 2.

(5) Expression of fibronectin in the two groups of placental samples was detected by conventional immunohistochemistry using mouse anti-human FN monoclonal antibody (purchased from DAKO, 1:50 diluted) and DAB as substrate. The results demonstrated that there was fibronectin band between the trophoblast and caduca, and also among the trophocytes in the control samples, while there was no fibronectin band outside the trophocytes of RSA patient's samples.

EXAMPLE 2

Determination of the level of antinuclear antibody in peripheral blood of early secondary RSA patients (1) Mixture of chromosome No. 2 derived from a plurality of men (generally more than 20) was prepared.

(2) The mixture of chromosome No. 2 was diluted to the concentration of 10 chromosomes per field of oil immersion objective by coating buffer (0.05M sodium carbonate buffer, pH 9.6) to coat polystyrene microplate (ELISA plate).

(3) 50 μl of a patient's serum diluted by different diluting factors (1:64, 1:128, 1:256, 1:512, 1:1024) by buffer (PBS buffer containing 0.1% bovine serum albumin, pH 7.4) was added to each reaction well. The reaction lasted for 30 minutes at 37° C. Then the reaction wells were rinsed by PBS buffer (pH 7.4) twice.

(4) 50 μl of mouse anti-human IgG antibody labeled with horse radish peroxidase (purchased from DAKO) was added into each reaction well. The reaction lasted for 30 minutes at 37° C. Then the reaction wells were rinsed by PBS buffer (pH 7.4) twice.

(5) 0.1 ml solution of substrate TMB (3,3',5,5'-Tetramethylbenzidine) which was freshly prepared by a conventional method was added into each reaction well. The reaction lasted for 10 to 30 minutes at 37° C.

(6) The OD value of each reaction well was read by microplate reader to determine the level of antinuclear antibody. Alternatively, the maximal diluting factor of serum at which the color reaction can still be observed by naked eye is deemed as the titer of antinuclear antibody.

If the color reaction can still be observed at a diluting factor of serum more than 1:64, it is clinically significant.

EXAMPLE 3

Case 1

The patient had been married for 17 years when she visited the doctor for RSA. Her first and second gestations during 1982-1996 were ended by artificial abortion on the 8th gestational week. She wanted a baby when she was pregnant in 1999 for the third time. However, on the 8th gestational week, the patient had abdominal pain and then bled from vagina. Ultrasonic detection showed the termination of the fetal development. Then the abortion happened. Artificial contraception had been carried out since then. Other possible causes of abortion had been excluded through examination. The level of antinuclear antibody in peripheral blood of the patient before treatment was 1:128 as determined according to the method in Example 2.

A solution of purified chromosome No. 2 derived from the spouse of the patient was subcutaneously injected to the patient for four times on Dec. 7, 1999, Jan. 14, Jan. 20 and Jan. 28, 2000 respectively. For the first three times, the topical reaction strength on the skin after injection was ++++. For the fourth time, the reaction strength was ++. The patient's level of antinuclear antibody in peripheral blood was 1:32 as determined after the fourth injection according to the method of Example 2.

The patient born a healthy boy baby weighed 2800 g in August 2001.

EXAMPLE 4

Case 2

The patient had been married for 4 years when she visited the doctor for RSA. Her first gestation in 1995 was ended by artificial abortion on the 7th gestational week. She wanted a baby when she was pregnant in August 1998 for the second time. However, on the 7th gestational week, the patient had abdominal pain and then bled from vagina. Ultrasonic detection showed the termination of the fetal development. Then the abortion happened. The patient got pregnant for the third and forth time in January 1997 and June 1997. Hematic secretion appeared in vagina on the 8th and 7th gestational week respectively. Traditional Chinese medicament containing gesterol had been used to protect the fetus from abortion and bleeding stopped. On the 10th gestational week, ultrasonic detection showed the termination of the fetal development. Drug abortion was performed. The dead fetus was about 8 gestational weeks old. Artificial contraception had been carried out since July 1997. The level of antinuclear antibody in peripheral blood of the patient before treatment was 1:1024 as determined according to the method in Example 2.

A solution of purified chromosome No. 2 derived from the spouse of the patient was subcutaneously injected to the patient for four times on Jun. 25, Jul. 12, Jul. 28 and Aug. 12, 1999 respectively. For the first three times, the topical reaction strength on the skin after injection was ++++. For the fourth time, the reaction strength was ++. The patient's level of antinuclear antibody in peripheral blood was 1:64 after the fourth injection as determined according to the method of Example 2.

The patient born a healthy boy baby weighed 3000 g in May 2000.

EXAMPLE 5

Case 3

The patient had been married for 5 years when she visited the doctor for RSA. Her first and second gestations during 1993-1995 were ended by artificial abortion on the 7th gestational week. She wanted a baby when she was pregnant in 1996 for the third time. However, on the 8th gestational week, the patient had abdominal pain and then bled from vagina. Ultrasonic detection showed the termination of the fetal development. Then the abortion happened. The patient got pregnant twice during 1997-1998. Hematic secretion appeared in vagina on the 7th gestational week of each gestation. Traditional Chinese medicament containing gesterol had been used to protect the fetus from abortion and bleeding stopped. On the 10th gestational week, ultrasonic detection showed the termination of the fetal development. Drug abortion was performed. The dead fetus was about 7 gestational weeks old. Artificial contraception had been carried out since January 1998. The level of antinuclear antibody in peripheral blood of the patient before treatment was 1:128 as determined according to the method in Example 2.

A solution of purified chromosome No. 2 derived from the spouse of the patient was subcutaneously injected to the patient for four times on Sep. 6, Sep. 12, Sep. 25 and Oct. 19, 1998 respectively. For the first three times, the topical reaction strength on the skin after injection was ++++. For the fourth time, the reaction strength was ++. The patient's level of antinuclear antibody in peripheral blood was lowered to 1:64 after the fourth injection.

The patient born a healthy boy baby weighed 2800 g in September 1999.

The invention claimed is:

1. A method of diagnosing immunological recurrent spontaneous abortion, comprising the steps of:
    determining a level of antinuclear antibody in a body fluid sample from a patient by a method involving contacting and reacting the sample with an isolated human chromosome No. 2 containing fibronectin encoding gene as antigen; and
    comparing the determined level with a level of the corresponding antinuclear antibody of a normal control; wherein a higher level of said antibody in said sample compared to the level of said antibody in a control is indicative of immunological recurrent spontaneous abortion.

2. A method of monitoring a therapeutic effect for immunological spontaneous abortion, comprising the steps of:
    determining a level of an antinuclear antibody in a body fluid sample from a patient, after a treatment, by a method involving contacting and reacting the sample with an isolated human chromosome No. 2 containing fibronectin encoding gene as antigen; and
    comparing the determined level with the corresponding level before the treatment;
    wherein a lower level of said antibody in said sample compared to the level before the treatment is indicative of a positive therapeutic effect of the treatment.

* * * * *